(12) United States Patent
Fukuda et al.

(10) Patent No.: US 7,372,050 B2
(45) Date of Patent: May 13, 2008

(54) METHOD OF PREVENTING CHARGING, AND APPARATUS FOR CHARGED PARTICLE BEAM USING THE SAME

(75) Inventors: Muneyuki Fukuda, Kokubunji (JP); Hiroyasu Shichi, Tokyo (JP); Satoshi Tomimatsu, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 231 days.

(21) Appl. No.: 11/258,911

(22) Filed: Oct. 27, 2005

(65) Prior Publication Data

US 2006/0060794 A1 Mar. 23, 2006

Related U.S. Application Data

(63) Continuation of application No. 10/773,330, filed on Feb. 9, 2004, now Pat. No. 6,977,376, which is a continuation of application No. 10/180,536, filed on Jun. 27, 2002, now Pat. No. 6,774,363.

(30) Foreign Application Priority Data

Nov. 15, 2001 (JP) .............................. 2001-349723

(51) Int. Cl.
*H01J 37/20* (2006.01)
(52) U.S. Cl. .................................. 250/492.21; 250/309
(58) Field of Classification Search ........... 250/492.21, 250/309, 398, 251
See application file for complete search history.

(56) References Cited

U.S. PATENT DOCUMENTS

| 5,012,109 A | 4/1991 | Shichi et al. |
|---|---|---|
| 5,512,746 A | 4/1996 | Saito |
| 5,591,971 A | 1/1997 | Shahar et al. |
| 6,303,932 B1 * | 10/2001 | Hamamura et al. ......... 250/309 |
| 6,354,438 B1 | 3/2002 | Lee et al. |
| 6,538,254 B1 * | 3/2003 | Tomimatsu et al. .... 250/442.11 |
| 6,664,552 B2 | 12/2003 | Shichi et al. |
| 6,794,663 B2 | 9/2004 | Shichi et al. |
| 6,818,891 B1 | 11/2004 | Hough et al. |
| 2002/0005481 A1 | 1/2002 | Williams |

FOREIGN PATENT DOCUMENTS

| JP | 7-74076 | 3/1995 |
|---|---|---|
| JP | 7-94562 | 4/1995 |
| JP | 8-138617 | 5/1996 |
| JP | 11-154479 | 6/1999 |
| JP | 2000-173525 | 6/2000 |
| JP | 2001/084947 | 3/2001 |

* cited by examiner

*Primary Examiner*—Kiet T. Nguyen
(74) *Attorney, Agent, or Firm*—Mattingly, Stanger, Malur & Brundidge, PC

(57) ABSTRACT

An apparatus for a charged particle beam has a charged particle source; a charged particle optical system for focusing and deflecting a charged particle beam emitted from the charged particle source; a detector for detecting secondary particles emitted from a sample irradiated with the charged particle beam; and a sample holder on which the sample is mounted. The apparatus has an electrode for preventing charging which is provided so as to be movable with respect to the surface of the sample holder, and a controller for the electrode for preventing charging, which controls a voltage to be applied to the electrode for preventing charging and the movement. Preventing the charging is performed by generating an induced current or a current between an area irradiated with the charged particle beam in the sample and the electrode for preventing charging.

10 Claims, 15 Drawing Sheets

METHOD OF PREVENTING CHARGING, AND APPARATUS FOR CHARGED PARTICLE BEAM USING THE SAME

This is a continuation application of U.S. Ser. No. 10/773, 330, filed Feb. 9, 2004 now U.S. Pat. No. 6,977,376, which is a continuation of U.S. Ser. No. 10/180,536, filed Jun. 27, 2002, which is now U.S. Pat. No. 6,774,363.

BACKGROUND OF THE INVENTION

The present invention relates to a charged particle beam technique for irradiating a sample with a charged particle beam, to observe, analyze, and process the sample.

An apparatus for a charged particle beam for irradiating a sample with a charged particle beam and observing, analyzing, and processing the sample is widely used. In the case where a sample contains an insulating material, when the surface of the sample is scanned with a charged particle beam, the surface of the sample may be charged. The charging disturbs observation, analysis, and processing due to drift of an emitted beam and decrease in a discharge amount of secondary particles. Consequently, a method of preventing the charging is important.

Conventional charging preventing methods include a method of preventing charging by irradiating the surface of a sample with a charged particle beam, a method of making charges escape by forming a conductive layer on the surface of a sample by irradiation of an ultraviolet ray or charged particle beam, a method of making charges escape by covering the surface of a sample with a conductive film, and a method of making charges escape by using conductive foil, conductive paste or a conduction terminal.

As a method of preventing charging by irradiation of a charged particle beam, there is, as prior art 1, "charged particle beam processing apparatus and method (Japanese Patent Application Laid-Open (JP-A) No. 8-138617)". The prior art 1 discloses an apparatus and method for detecting secondary electrons from the surface of a sample without extracting electrons emitted from an electron gun for preventing charging by a secondary electron detector by disposing the nozzle-shaped tip of the electron gun near the surface of the sample at the time of preventing charging of the sample with an ion beam, by using an electron beam.

The method of making charges escape by forming a conductive layer on the surface of a sample by irradiation with an ultraviolet ray or charged particle beam includes, as prior art 2, "secondary electron image detecting method and apparatus, and processing method and apparatus using focusing charged particle beam (JP-A-11-154479)" and "charged particle beam processing apparatus and method (JP-A-8-138617)". The prior art 2 discloses an apparatus and method realizing processing of 1.0 µm or less in such a manner that charging is stably avoided irrespective of the state and kind of a sample, a secondary electron image of the sample is detected at high resolution in a real time manner, and observation of the pattern of the sample, positioning of the focused charged particle beam, and the like are realized with high accuracy by the method of inducing a conductive layer and making charges escape by irradiating a region including a focused charged particle beam irradiation region on the surface of a sample with a positive ion beam.

As the method of covering the surface of a sample with a conductive film, there is, as prior art 3, "method of manufacturing conductive resist film and semiconductor device (JP-A-7-74076)". The prior art 3 discloses a method of suppressing charging as much as possible by a method of forming a conductive film under a resin film which is sensitive to charged particles and a method of exposing a pattern with high accuracy while reducing a charged particle beam curved irradiation phenomenon.

The method of making charges escape by a conductive terminal includes, as prior art 4, "sample charging eliminating apparatus (JP-A-2000-173525)". The prior art 4 discloses an apparatus preventing hindrances to observation, analysis, and processing due to a charging phenomenon and realizing a high-sensitivity, high-resolution, and high-precision work by making charges generated during the process of observation, analysis, and processing escape via an earth line by allowing a terminal to come into contact with the periphery of at least 180 degrees of an observation, analysis, and processing region by a remote control.

The method of capturing charges by a conductive probe includes, as prior art 5, "micropattern measuring apparatus (JP-A-7-94562)". The prior art 5 discloses a micropattern measuring apparatus which prevents a charge-up phenomenon in such a manner that negative charges generated by an electron beam are captured either by directly contact of a probe with a micropattern or by applying a positive voltage of 5000V to a probe from a position apart from the micropattern by 30 µm.

According to the prior arts, by the method of covering the surface of a sample with a conductive substance or making a conductive substance come into contact with the surface of a sample, the method of irradiating the surface of a sample with a charged particle beam, or the like, charging which occurs at the time of irradiating the sample with a charged particle beam is eliminated.

According to the charging preventing methods of the prior arts 1 and 2, if the irradiation amount of an electron or ion beam used for preventing charging does not coincide with that of the charged particle beam used for observation, analysis, and processing, charging occurs. In this case, to improve resolution of an observed image by improving the precision of an irradiation position of a charged particle beam and to improve contrast of an observation image by increase in an emission amount of secondary electrons generated by irradiation of the charged particle beam, the irradiation amount of an electron or ion beam has to be controlled by means for detecting a charging preventing condition by using a reference. Further, control of the irradiation amount by the charging preventing condition detecting means requires experience of the operator.

Further, secondary electrons emitted by irradiation with an electron or ion beam are detected by a secondary electron detector. At this time, the secondary electrons overlap with secondary electrons emitted from the surface of a sample irradiated with the charged particle beam, so that the secondary electrons emitted by the irradiation of the electron or ion beam deteriorate an observation image very much. In order to suppress an emission amount of the secondary electrons emitted by the irradiation of the electron or ion beam, the irradiation amount has to be regulated. When a charging amount of the surface of a sample is large, the charging preventing method by irradiation of an electron or ion beam is not effective.

Generally, secondary electrons generated by the irradiation of a charged particle beam are emitted 10 to 100 times as much as secondary ions. Consequently, the resolution of an observation image based on a secondary electron signal is higher than that of an observation image based on secondary ions. However, in the case of emitting an electron or ion beam in order to prevent charging, due to generation of secondary electrons, the resolution of an observation image based on the secondary electron signals deteriorates more than that of an observation image based on secondary ions. Therefore, in the apparatus for a charged particle beam, a secondary ion detector is widely used.

In the charging preventing method of the prior art 3, a coating with a conductive layer is formed on the surface of a sample. When the surface of a sample is covered, however, the structure of the surface cannot be observed with a charged particle beam, and a problem occurs in determination of a position of observation, analysis, and processing with a charged particle beam. Further, in order to avoid contamination of a sample, the charging preventing film formed on the surface of the sample has to be removed after observation, analysis, and processing with the charged particle beam.

According to the method of making charges escape by the conductive terminal disclosed in the prior art 4, the terminal has to be made come into contact with the periphery of at least 180 degrees of the region of observation, analysis, and processing by a remote control. By making the terminal come into contact with the periphery of at least 180 degrees of the region of observation, analysis, and processing, it becomes difficult to recognize the contact of the terminal and, simultaneously, positioning precision in the state where the terminal is in contact deteriorates. Further, a region wider than the observation, analysis, and processing region irradiated with the charged particle beam is contaminated by the contact of the terminal.

According to the method of capturing charges by the conductive probe disclosed in the prior art 5, when the probe is in contact, the probe hides a part of a micropattern, so that the micropattern cannot be observed. In the case where the probe is not in contact, an observation image is distorted by a strong electric field generated when charged electrons are captured by the probe.

In the case of fabricating a sample by using a charged particle beam without employing the charging preventing method, the operator has to perform observation, analysis, and processing by relying on a drifting observation image. Since operations and setting are visually recognized, a work of performing the observation, analysis, and processing without using the charging preventing method requires skill. When the operator fails in the processing, the sample may be destroyed. When the operator fails in a probe operation, the sample or the tip of the probe may be destroyed.

The above methods have subjects such as reduction in contamination of a sample, lessening of a work of covering the surface of a sample with the conductive substance or making the conductive substance contact with the surface, reduction in charges newly generated by irradiation of the surface of a sample with a charged particle beam and an influence of the terminal onto observation, analysis, and processing using secondary electrons, and elimination of a skill to directly extract a sample piece from a sample.

SUMMARY OF THE INVENTION

The present invention has been achieved in consideration of the above and its object is to provide a very reliable method of preventing charging without requiring experience or skills to suppress charging in the surface of a sample and to provide an apparatus for a charged particle beam having generally excellent analysis and sample fabricating efficiency.

The present invention provides, as means achieving the object, a technique based on novel finding such that charging which occurs when a sample is irradiated with a charged particle beam (ion beam, electron beam, or the like) is controlled by an electrode for preventing charging provided adjacent to or in contact with the irradiated area.

Even when the electrode for preventing charging and the irradiated area are electrically insulated from each other, when the area is irradiated with a charged particle beam, a current induction occurs between the charged irradiated area and the electrode for preventing charging for the following reason. By efficiently extracting secondary particles emitted from the surface of the sample charged by the irradiation of the charged particle beam by the electrode for preventing charging, a current induction occurs between the electrode for preventing charging and the irradiated area. When the electrode for preventing charging is provided within, for example, 300 μm from the irradiated area or in contact with the irradiated area, by the irradiation of the charged particle beam, a current flows between the charged irradiated area and the electrode for preventing charging.

When the operator performs observation, analysis, processing, and probe operation of high precision, the interval between the electrode for preventing charging and the irradiated area has to be further reduced. As the interval is reduced, the charging voltage decreases by the induced current or the generated current between the electrode and the irradiated area, and an electric field near the irradiated area generated by the charging can be confined in a narrower space. As a result, the irradiation position of the charged particle beam in the surface of the insulating sample can be controlled with position precision of about 1/50 times of the interval. Simultaneously, a secondary particle detection amount in a secondary particle detector is not influenced by charging, so that a clear observation image can be obtained.

Representative configuration examples of a method of preventing charging and an apparatus for a charged particle beam using the method of the invention realizing observation, analysis, processing, and probe operation of high precision by using the technique of preventing charging will be described hereinbelow.

First, the invention provides a method of preventing charging, including the steps of irradiating a sample mounted on a sample holder with a charged particle beam emitted from a charged particle beam source, and applying a predetermined voltage to an electrode for preventing charging disposed near a surface of the sample holder to generate an induced current between the electrode for preventing charging and an irradiated area in which charging occurs in the sample, thereby executing a control of preventing the charging without contact with the sample.

The invention also provides a method of preventing charging, including the steps of irradiating a sample mounted on a sample holder with a charged particle beam emitted from a charged particle beam source, applying a predetermined voltage to an electrode for preventing charging disposed near a surface of the sample holder, and making the electrode come into contact with the sample to generate a current between the electrode for preventing charging and an irradiated area in which charging occurs in the sample, thereby executing a control of preventing the charging.

The invention provides an apparatus for a charged particle beam, having: a charged particle source; a charged particle optical system for focusing and deflecting a charged particle beam emitted from the charged particle source; a detector for detecting secondary particles emitted from a sample irradiated with the charged particle beam; and a sample holder on which the sample is mounted, the apparatus including: an electrode for preventing charging which is provided so as to be movable with respect to the surface of the sample holder;

and a controller for the electrode for preventing charging, for controlling a voltage to be applied to the electrode for preventing charging and the movement, wherein a control for preventing the charging is performed by generating an induced current or a current between an irradiated area in the sample, which is irradiated with the charged particle beam, and the electrode for preventing charging.

The invention also provides an apparatus for a charged particle beam, having: a charged particle source; a lens for focusing a charged particle beam emitted from the charged particle source; a deflector; a detector for detecting secondary particles emitted from a sample irradiated with the charged particle beam; a sample holder for holding the sample, and a sample position controller for controlling the position of the sample holder, the apparatus being provided with: a first electrode which is provided between a charged particle beam irradiated area in the sample and the lens so as to be movable with respect to the sample and which generates an induced current or a current between the first electrode and the charged particle beam irradiated area; an electrode controller controlling the first electrode, and driving independent of the sample holder position controller; and a second electrode driving independent of the sample holder position controller and generating a current between the second electrode and the charged particle beam irradiated area, wherein a control of preventing charging in the charged particle beam irradiated area which is charged is performed by using the first and second electrodes.

DETAILED DESCRIPTION OF THE PREFERRED EMBODIMENTS

First Embodiment

Figure 1:
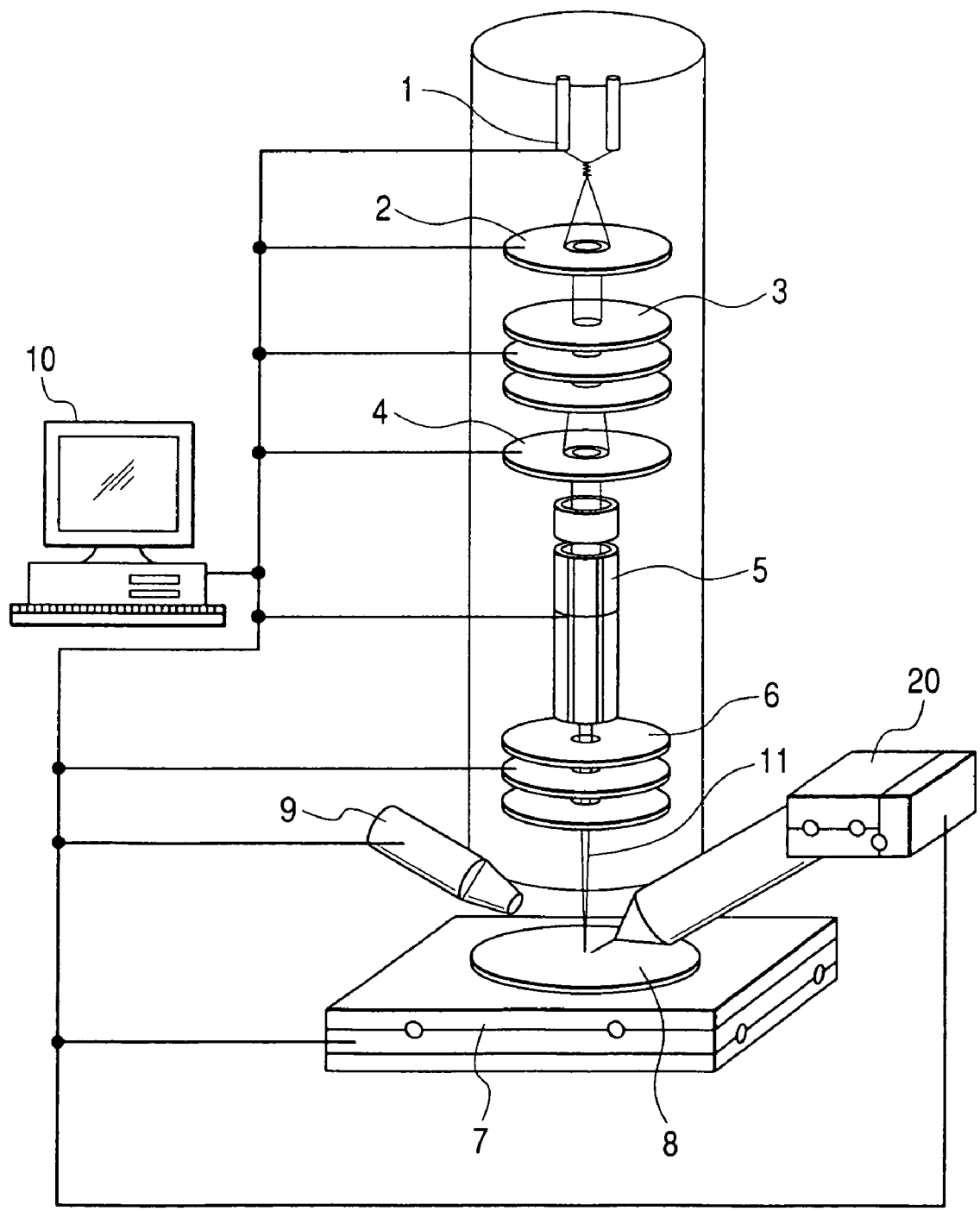
FIG. 1 is a diagram showing a first embodiment of an apparatus for a charged particle beam according to the invention.

FIG. 1 shows a basic configuration of a first embodiment of an apparatus for a charged particle beam according to the invention.

The apparatus for a charged particle beam of the invention includes a charged particle optical system for extracting an ion beam 11 by an electrode 2 from an ion source 1, condensing the ion beam 11 by a condenser lens 3, narrowing the ion beam 11 by an aperture 4, and focusing the ion beam 11 onto the surface of a sample 8 by an objective lens 6, a movable sample holder 7 on which a sample is mounted, a secondary particle detector 9, a deflector 5, a controller 10, and an electrode 20 for preventing charging.

The electrode 20 for preventing charging takes the form of an electrode made of a conductive material. The tip portion of the electrode 20 for preventing charging approaches an ion beam irradiation position of the sample 8 by in-plane position measuring means for making observation by scanning with an ion beam and height position measuring means using a set value of the objective lens 6.

When the sample is irradiated with an ion beam, the ion beam undergoes elastic scattering or inelastic scattering. In the case of the inelastic scattering; secondary electrons are generated from the sample. Many of the secondary electrons have energy of only a few eV. When the surface of the ion beam irradiated area is positively charged by a few V, low-speed secondary electrons cannot be liberated and remain in the sample. When an ion beam irradiation current and all of currents flowing out from the sample become equal to each other, the surface potential of the sample reaches equilibrium.

Figure 2:
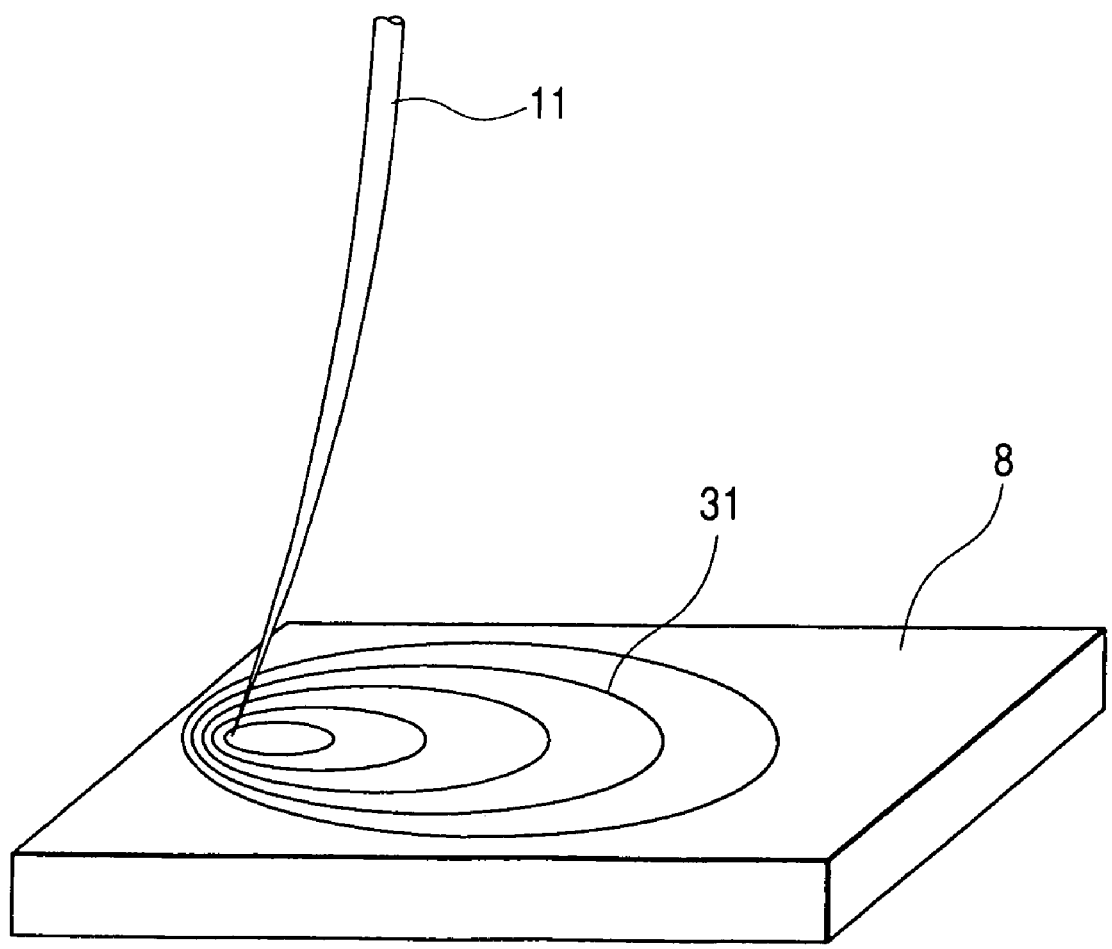
FIG. 2 is a diagram showing sample charging and beam drift at the time of irradiation of an ion beam.

FIG. 2 shows a state where the ion beam drifts in the direction of the arrow due to unbalance of a potential distribution of a sample. In the diagram, 31 denotes equipotential lines. Due to the irradiation position of the ion beam 11, a dielectric constant distribution in the surface of the sample 8, and the like, the surface potential is distributed in a deflected way with respect to the ion beam. The charges flow out against insulating resistance toward the sample holder. It is considered that the insulating resistance is related to volume resistance and surface resistance of the sample. In an insulator, the surface resistance often becomes lower than the volume resistivity.

Change in time $dVc/dt$ of a charged potential $Vc$ of a positive charge in the ion beam irradiated area is expressed by the following equation where C denotes an effective capacitance of the surface of a sample, R denotes insulation resistance, and Ip indicates a beam current.

$$dVc/dt = Ip/C - Vc/RC$$

Figure 3:
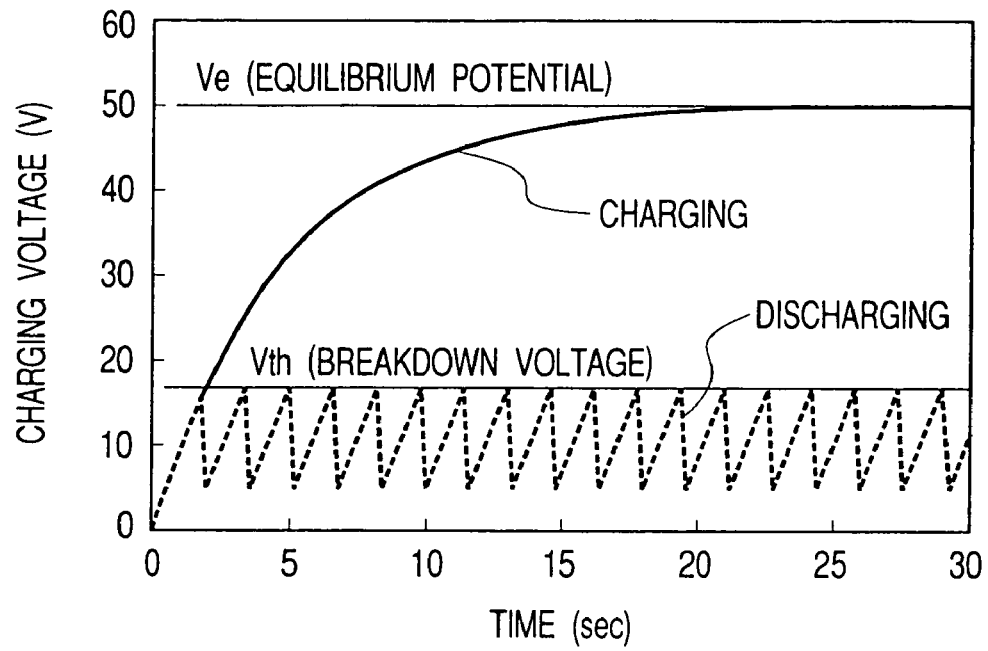
FIG. 3 is a diagram showing dependency on ion beam irradiation time of a charging voltage to the surface of a sample.

FIG. 3 shows dependency on time of charging voltage in the ion beam irradiation position when it is assumed that an ion beam irradiation amount (beam current) is 10 nA, effective capacitance of the surface of the sample is 1 nF, and insulation resistance is 5 GΩ. As time elapses, the charging voltage increases and almost equilibrium is reached after about 10 seconds.

If charging is performed and the equilibrium is reached, an influence is hardly exerted to ion beam fabrication. When a change occurs with time in the surface potential at the time of irradiation of an ion beam, a beam drift occurs. The beam drift is caused by deflection of the surface potential distribution due to the structure of the sample surface or property values. For example, the surface of a cover glass (30 mm×20 mm, having a thickness of 0.1 mm) was irradiated with a scan ion beam, and a change with time of an observation image was evaluated by a method of detecting secondary particles. When an SIM image was observed, the observation area in the SIM image was repeatedly moved. If the potential of the sample reaches the equilibrium after predetermined time of the irradiation of the ion beam, it is supposed that the observation area does not shift. However, in reality, the observation area shifts repeatedly. It can be therefore said that a change occurs with time in the potential in the surface of a sample due to repetition of discharging and charging.

Figure 4:
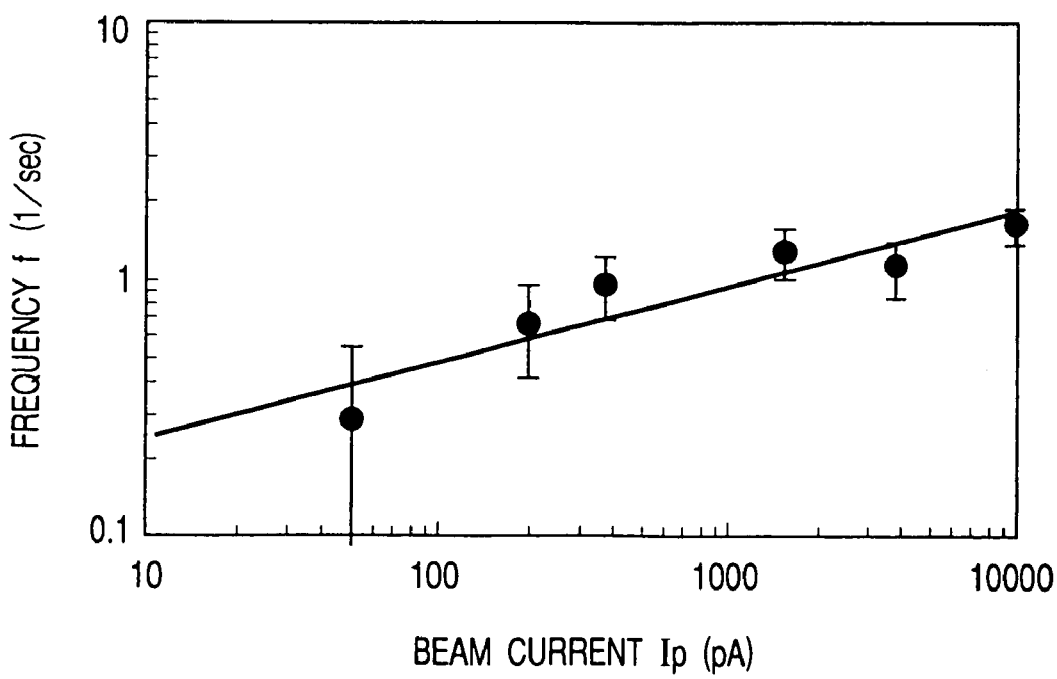
FIG. 4 is a diagram showing dependency on a beam current of a beam frequency by charging vibration.

FIG. 4 shows dependency of the beam current of the frequency of the observation area shift. The frequency "f" of discharging increases as the beam current Ip increases. When the beam current increases, as vibration caused by charging increases, a beam drift also increases.

Figure 5:
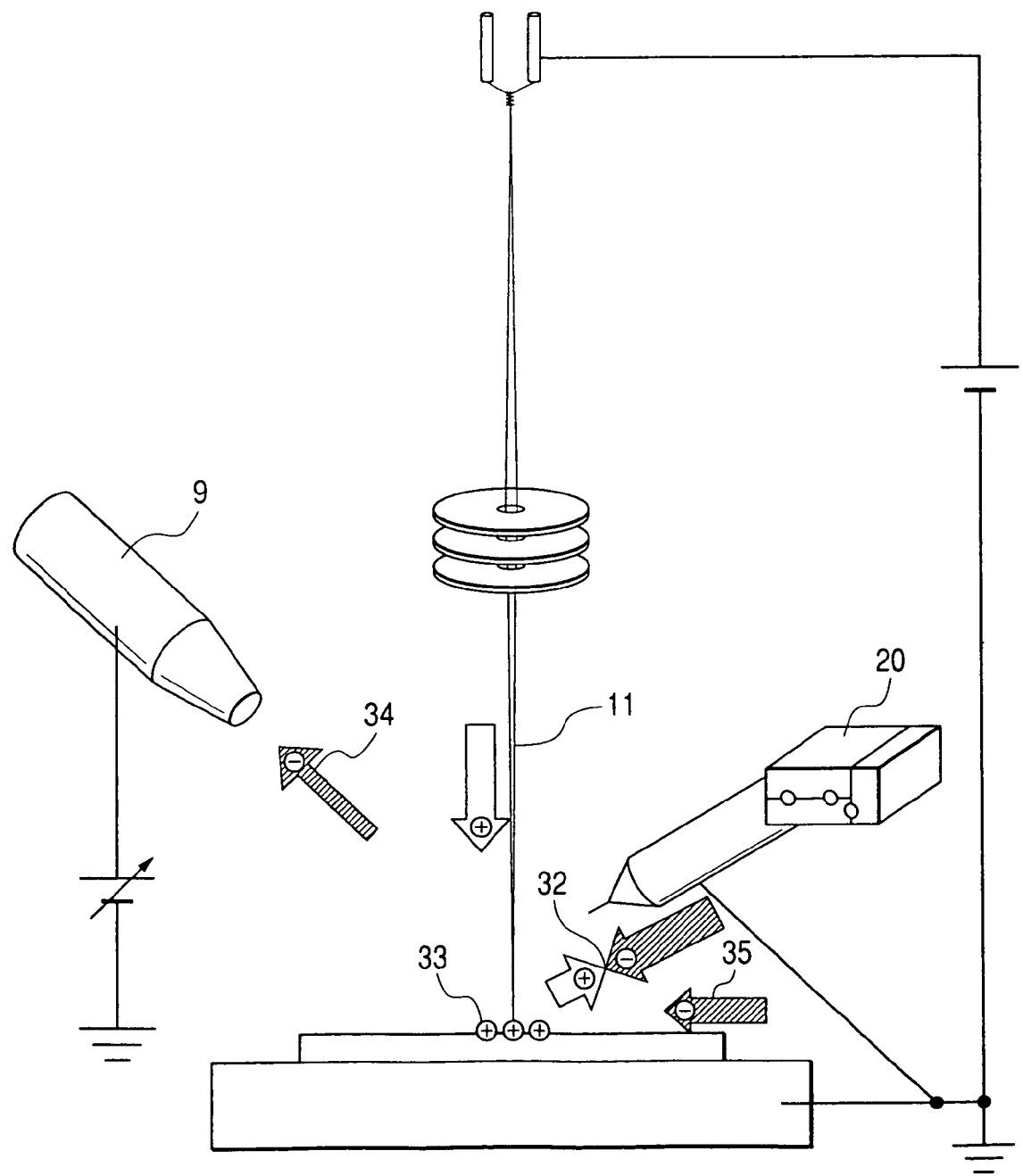
FIG. 5 is a circuit diagram showing a method of controlling charging by an electrode for preventing charging.

FIG. 5 is a circuit diagram showing a method of controlling charges 33 generated by irradiation of an ion beam by the electrode 20 for preventing charging. By making the tip of the electrode 20 for preventing charging approach the surface of a sample which is charged by irradiation of an ion beam, charge exchange 32 can be performed. The tip of the electrode 20 for preventing charging is a needle-shaped electrode made of a conductive material. A current flowing by the charge exchange 32 by the electrode 20 for preventing charging becomes 60 percent of the ion beam current or more when the tip of the electrode 20 for preventing charging is fixed in the position apart from the irradiation area in the surface of the sample by 30 µm in the horizontal direction and 30 µm in the vertical direction.

Figure 6:
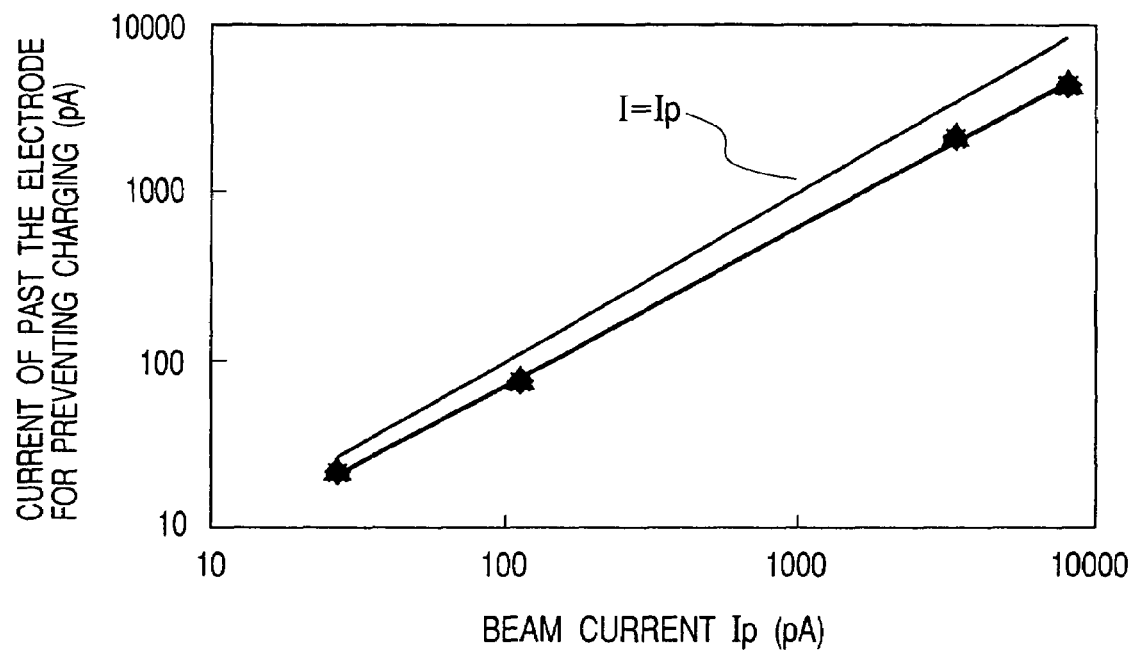
FIG. 6 is a diagram showing dependency on the irradiation current of a current flowing in the electrode for preventing charging.

The electrode 20 for preventing charging always supplies electrons for preventing positive charges generated by the irradiation of the ion beam. FIG. 6 shows dependency of the beam current of a current (hereinbelow, supplied current) passed to the electrode 20 for preventing charging when the cover glass charging control is performed.

The tip of the electrode 20 for preventing charging was disposed adjacent to a position apart from the ion beam irradiated position by about 16 µm, and a supplied current was measured while changing the beam current within the range from 20 pA to 8 nA. In the graph, the result of measurement is indicated by the signs ■. A thin straight line shows the case where the supplied current I is equal to the beam current Ip. From the two straight lines in FIG. 6, it is understood that most of the beam current Ip flows into the electrode 20 for preventing charging, the amount of the supplied current I is proportional to the beam current Ip, and a current flowing out from the sample against insulation resistance in a path other than the electrode 20 for preventing charging is also almost proportional to Ip. In this case, the insulation resistance does not depend on the beam current.

Figure 7:
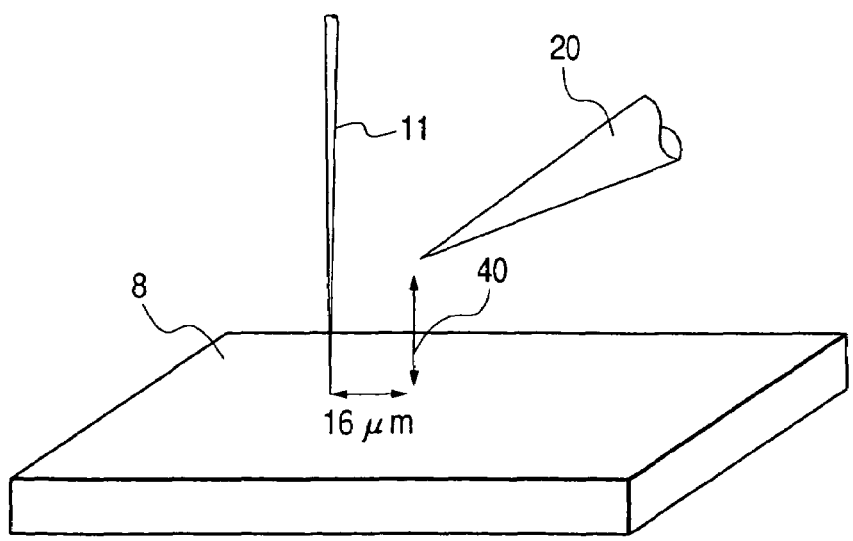
FIG. 7 is a diagram showing the height of the tip of the electrode for preventing charging from a sample.

FIG. 7 shows the height of the tip of the electrode 20 for preventing charging from the sample. When an area of 32×32 µm$^2$ is irradiated with a beam current of 8.0 nA, the tip of the electrode 20 for preventing charging is set to a height of 2 µm and in the position apart from the center of the irradiation position by 16 µm in the lateral direction, and only the height is changed to 40 µm. In the case of changing the height of the electrode 20 for preventing charging, an influence of the controller is exerted, so that the amount of shift in the lateral direction is set to about 100 µm at the maximum.

Figure 8:
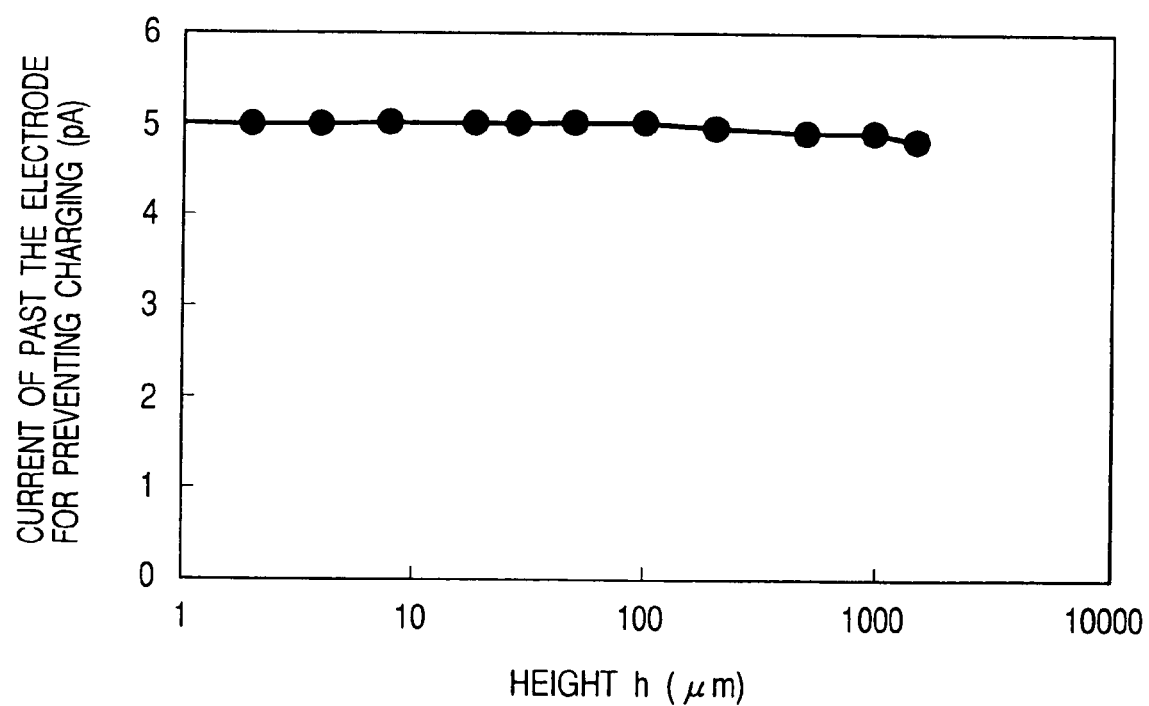
FIG. 8 is a diagram showing dependency on the height of the tip of a current flowing in the electrode for preventing charging with an ion beam.

FIG. 8 shows a result of measurement of dependency on the height of a current flowing in the electrode for preventing charging. Although the current flowing in the electrode for preventing charging changes in the range from 4.4 to 5.1 nA, it does not depend on the height up to 100 µm.

On the other hand, many of secondary electrons emitted from the surface of the sample by the irradiation of the ion beam 11 have an energy of only a few eV. In this case, low-speed secondary electrons cannot be liberated and remain in the sample to charging and an electric field generated by the electrode 20 for preventing charging, so that the secondary particle detector 9 cannot detect the secondary electrons emitted from the sample. Further, the ion beam 11 is shifted by the electric field generated by the electrode 20 for preventing charging and the charging.

In order to solve the problem, a voltage source for applying a voltage to the charging preventing electrode itself, and the electrode 20 for preventing charging whose conductive tip has an elongated needle shape are provided. As shown in FIG. 5, when a negative potential is applied to the electrode 20 for preventing charting in a state where the surface of the sample is positively charged, an emission amount of secondary electrons 34 is increased in addition to the charge exchange with a charged area. When the electrode 20 for preventing charging applies a positive potential of about 2V to thereby lessen returning of the secondary electrons by charging, precision of ion beam scanning is improved and the detection of the secondary particle detector 9 of secondary electrons emitted from the surface of the sample is improved. Thus, the resolution of the observation image is improved twice as higher as that in the case of applying 0V to the electrode 20 for preventing charging.

Second Embodiment

Figure 9:
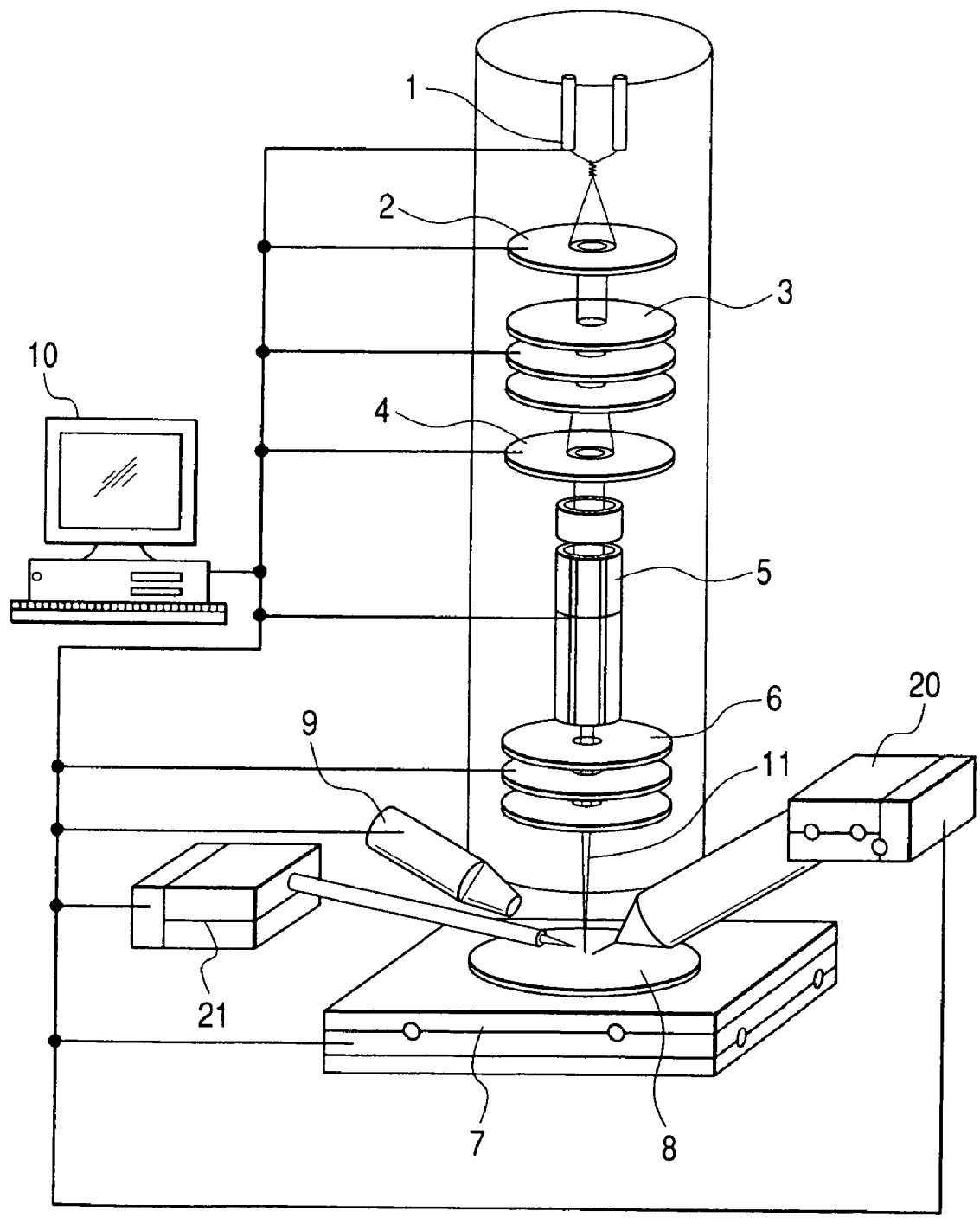
FIG. 9 is a diagram for explaining a second embodiment of the apparatus for a charged particle beam according to the invention.

FIG. 9 shows a basic configuration of a second embodiment of an apparatus for a charged particle beam according to the invention. In the embodiment, by assembling a probe manipulator 21, an apparatus for a charged particle beam for fabricating a sample of the order of a few µm to a sub µm is constructed.

The apparatus for a charged particle beam of the second embodiment includes the charged particle optical system for extracting the ion beam by the extraction electrode 2 from the ion source 1, condensing the ion beam 11 by the condenser lens 3, narrowing the ion beam 11 by the aperture 4, and focusing the ion beam 11 onto the surface of the sample 8 by the objective lens 6, the movable sample holder 7 on which a sample is mounted, the secondary particle detector 9, the deflector 5, the controller 10, the electrode 20 for preventing charging, and the probe manipulator 21.

The tip portion of the electrode 20 for preventing charging takes the form of a conductive needle having a radius of curvature of about 100 µm and is allowed to approach the surface of the sample 8. The electrode 20 for preventing charging is fixed in the position apart from the ion beam irradiated area by about 30 μm in the horizontal direction in the surface of the sample and by about 30 μm in the vertical direction. In the case where the sample contains an insulator to thereby positively charge the irradiated area, charges are exchanged with the irradiated area charged by the electrode 20 for preventing charging, thereby suppressing charging. In the case of performing a scan with an ion beam of 30 μA, a clear observation image can be obtained from the signal of the secondary particle detector 9.

However, in the case of emitting an ion beam of 10 nA to process a sample, charging increases, so that the ion beam irradiation position becomes uncontrollable. Consequently, a scan is performed with an ion beam of 30 pA and the tip of the probe manipulator 21 is made come into contact with the surface of a sample on the basis of the observation image. Also by emitting an ion beam of 10 nA at this time, the probe manipulator 21 suppresses charging by inflow of a near current to a portion between the probe manipulator 21 and the charged irradiated area, and can accurately control the ion beam irradiation position.

Figure 10:
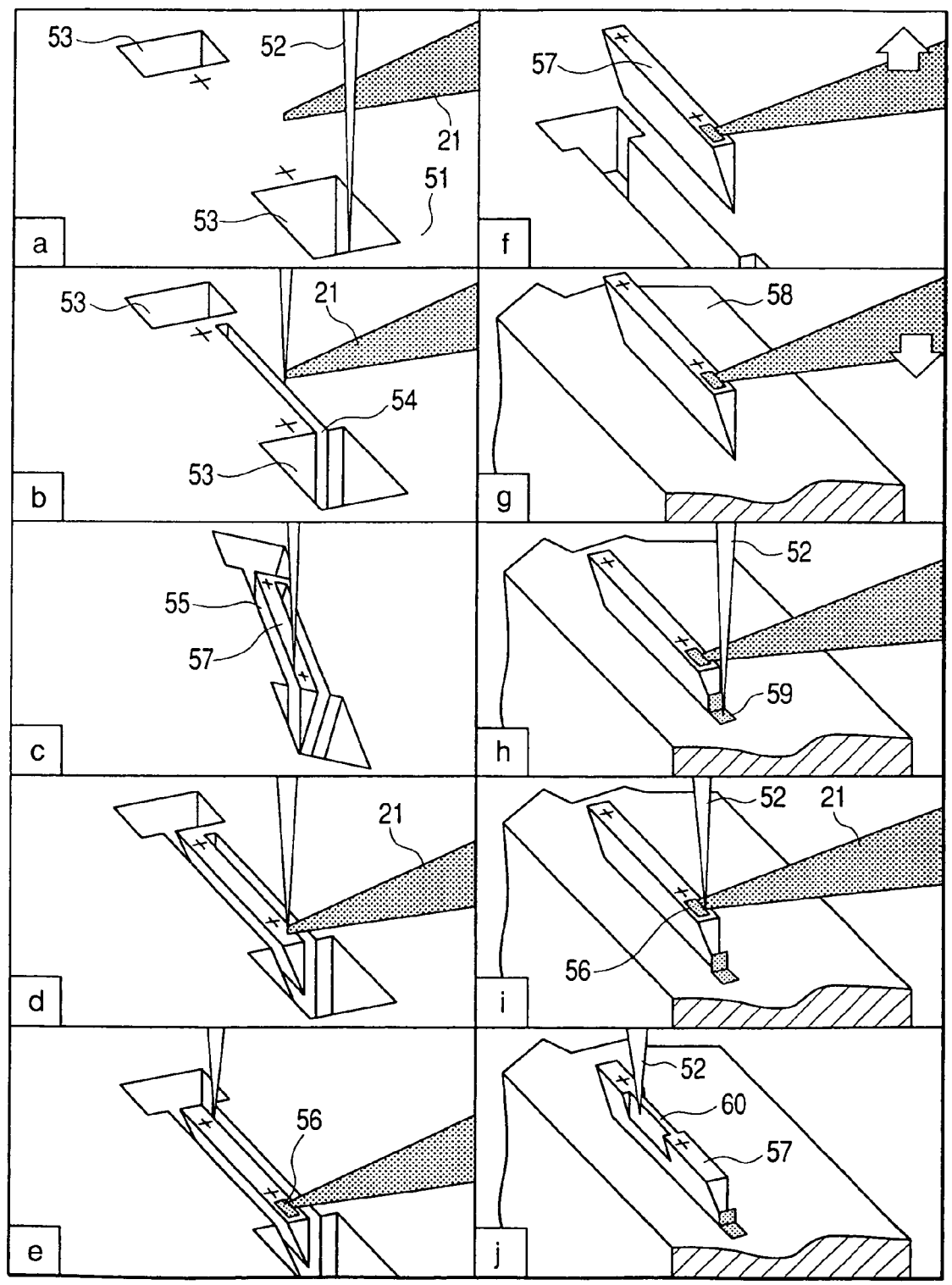
FIGS. 10a to 10j are diagrams showing a method of fabricating a high-precision analysis sample from an insulating material.

FIGS. 10-a to 10-j show a method of fabricating a high-precision analysis sample from an insulator.

In a state where the tip of the probe manipulator 21 is in contact with the surface of a sample, the posture of a substrate 51 is maintained so that the surface of the sample substrate 51 is irradiated with an ion beam 52 at the right angle, and the ion beam 52 scans in a rectangular shape over the substrate 51 so as not to be overlapped with the probe manipulator 21 to form a rectangular hole 53 having a required depth in the surface of the sample (FIG. 10-a) At this time, a voltage of +1V is applied to the probe manipulator 21. A desired sample position in an observation image can be clearly observed, fabrication is accurately set, and a specimen can be fabricated at high precision.

Subsequently, a vertical groove 54 is formed (FIG. 10-b). After moving the tip of the probe manipulator 21 away from the substrate 51, the substrate 51 is tilted so that the axis of the ion beam 52 with respect to the surface of the substrate 51 is tilted by about 30°, thereby forming a tilted groove 55. The tilt angle of the substrate 51 is changed by the sample holder (FIG. 10-c). The posture of the substrate 51 is reset to a state where the surface of the substrate 51 is perpendicular to the ion beam 52 and, after that, the tip of the probe manipulator 21 is made come into contact with a portion which becomes a sample in the substrate 51 (FIG. 10-d). The tip portion of the electrode 20 for preventing charging in the apparatus of FIG. 9 takes the form of a conductive needle having a radius of curvature of about 100 μm. The electrode 20 for preventing charging simultaneously takes the form of a gas nozzle for supplying a deposition gas and is allowed to approach the surface of the sample 8. The deposition gas is supplied from the gas nozzle, and an area including the tip portion of the probe manipulator 21 is locally irradiated with the ion beam 52, thereby forming an ion beam assist deposition (hereinbelow, abbreviated as IBAD) film 56. A specimen 57 as a separated portion of the substrate 51 and the tip of the probe manipulator 21 which are in contact with each other are connected via the IBAD film 56 (FIG. 10-e).

The rest portion is cut with the ion beam 52 to cut the specimen 57 out from the substrate 51. The cut specimen 57 is supported by the connected probe manipulator 21 (FIG. 10-f). The specimen 57 is moved to a mesh holder 58 (FIG. 10-g). A deposition gas is supplied from the gas nozzle and the boundary area in which the specimen 57 and the mesh holder 58 are in contact with each other is locally irradiated with the ion beam 52, thereby forming an IBAD film 59 (FIG. 10-h). An area adjacent to the IBAD film 56 is locally irradiated with the ion beam 52 to separate the probe manipulator 21 from the specimen 57 (FIG. 10-i). The observation area in the specimen 57 is thinned with the ion beam 52 to form a thin film having a thickness of about 10 nm. The sample can be therefore observed and analyzed at a resolution of the order of sub nm by a transmission electron microscope (FIG. 10-j).

Third Embodiment

Figure 11:
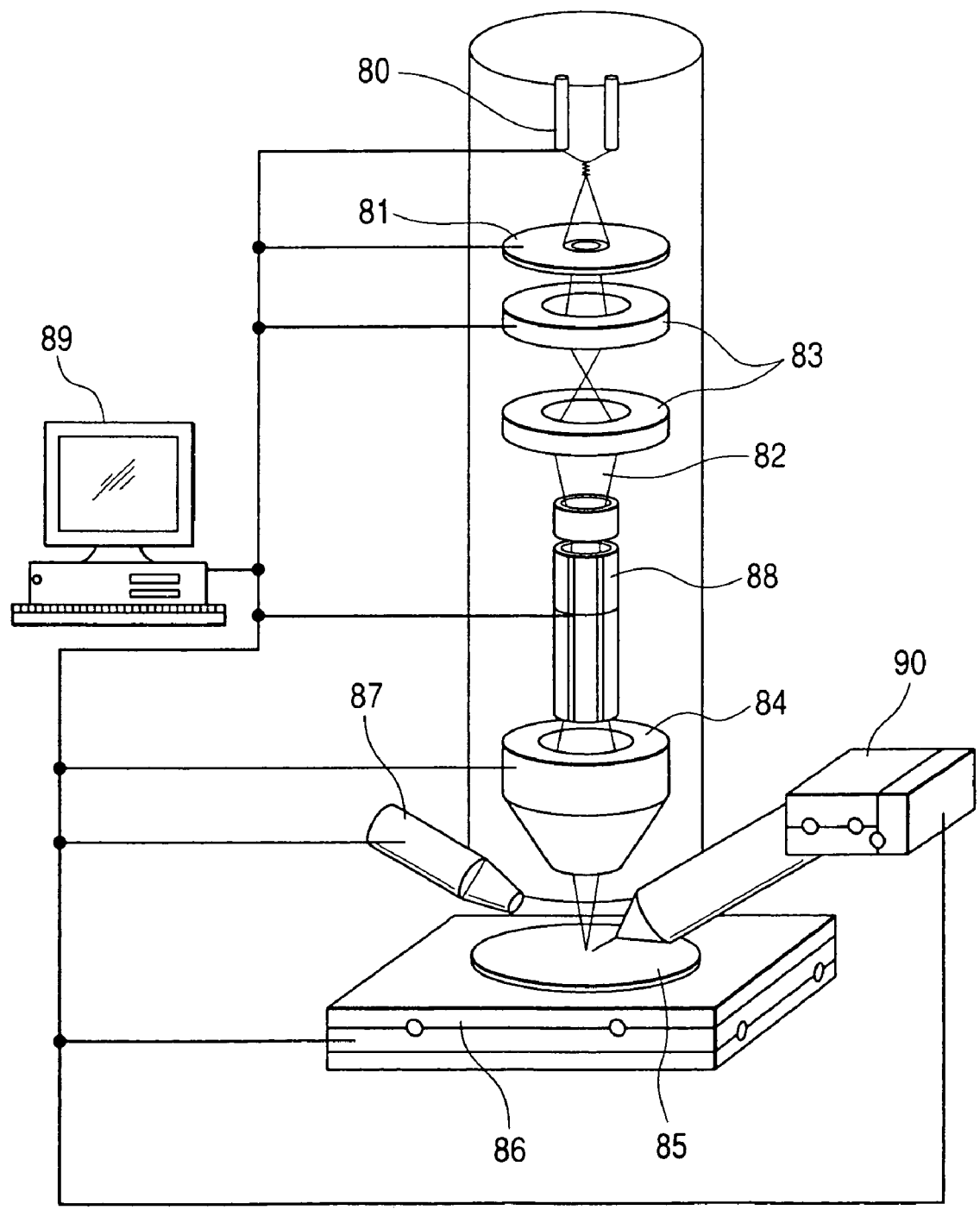
FIG. 11 is a diagram for explaining a third embodiment of the apparatus for a charged particle beam according to the invention.

FIG. 11 shows a basic configuration of a third embodiment of an apparatus for a charged particle beam of the invention.

The apparatus for a charged particle beam of the invention includes a charged particle optical system for extracting an electron beam 82 by an extraction electrode 81 from an electron source 80, condensing the electron beam 82 by a condenser lens 83, and focusing the electron beam 82 onto the surface of a sample 85 by an objective lens 84, a movable sample holder 86 on which the sample 85 is mounted, a secondary electron detector 87, a deflector 88, a controller 89, and an electrode 90 for preventing charging.

If the sample 85 contains an insulating material, an area irradiated with the electron beam 82 may be charged. Most of secondary electrons emitted from the surface of a sample by the irradiation of the electron beam 82 have an energy of only a few eV. When the secondary electrons are positively charged, they cannot be liberated from the sample and remain in the sample. When the secondary electrons are negatively charged, they are accelerated, so that the secondary electron detector 87 cannot detect secondary electrons from the sample 85. Further, the electron beam 82 is shifted by an electric field generated by charging, so that the irradiation position of the electron beam 82 cannot be controlled.

In an observation image of an insulator sample ($SiO_2$), the resolution severely deteriorates by a scan with the electron beam 82 (700 pA) of an accelerating voltage 2 kV. The cause is negative charging of the irradiation area.

Figure 12:
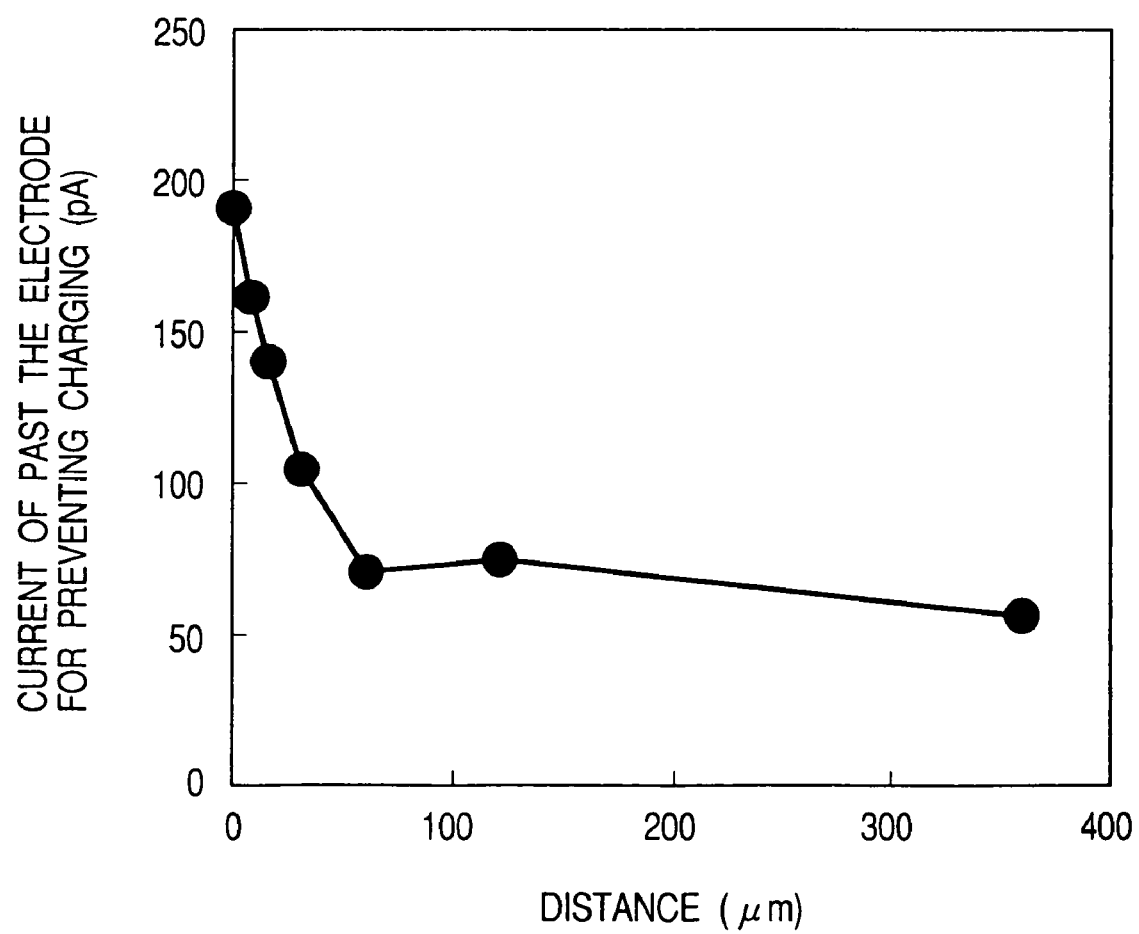
FIG. 12 is a diagram showing dependency of the height of the tip of a current flowing in the electrode for preventing charging with an electron beam.

FIG. 12 shows a current which flows by charge exchange between the electrode 90 for preventing charging and the charged irradiated area. In this case, the tip of the electrode 90 for preventing charging is moved apart from an irradiated area of 3×3 μm² by 9 μm in the horizontal direction and by 0 to about 360 μm in the vertical direction. When the tip of the electrode 90 for preventing charging is allowed to come into contact with the surface of the insulating material of the sample, a current of about 200 pA flows between the electrode 90 for preventing charging and the charged irradiated area. In the case where a current of 100 pA or higher flows in the electrode 90 for preventing charging, the resolution of the observation image reaches 1 nm.

Further, in the case of applying the voltage of +5V to the electrode 90 for preventing charging, a current of 500 pA flows when the tip of the electrode 90 is in the position in the surface of the sample, and a current of about 300 pA flows when the tip of the electrode 90 is in the position of the distance of 360 μm in the vertical direction. When the irradiated area is negatively charged and a positive voltage is applied, secondary electrons emitted from the surface of the sample by the irradiation of the electron beam 82 are captured by the electrode for preventing charging. As a result, the secondary electron detector 87 cannot detect the secondary electrons, so that the S/N ratio of the observation image deteriorates. In order to avoid capture of the secondary electrons by the electrode 90 for preventing charging and acceleration, it is sufficient to apply a negative voltage of 0V to −5V to the electrode 90. By the application, the S/N ratio of the observation image is improved, and the resolution reaches 1 nm.

Fourth Embodiment

Figure 13:
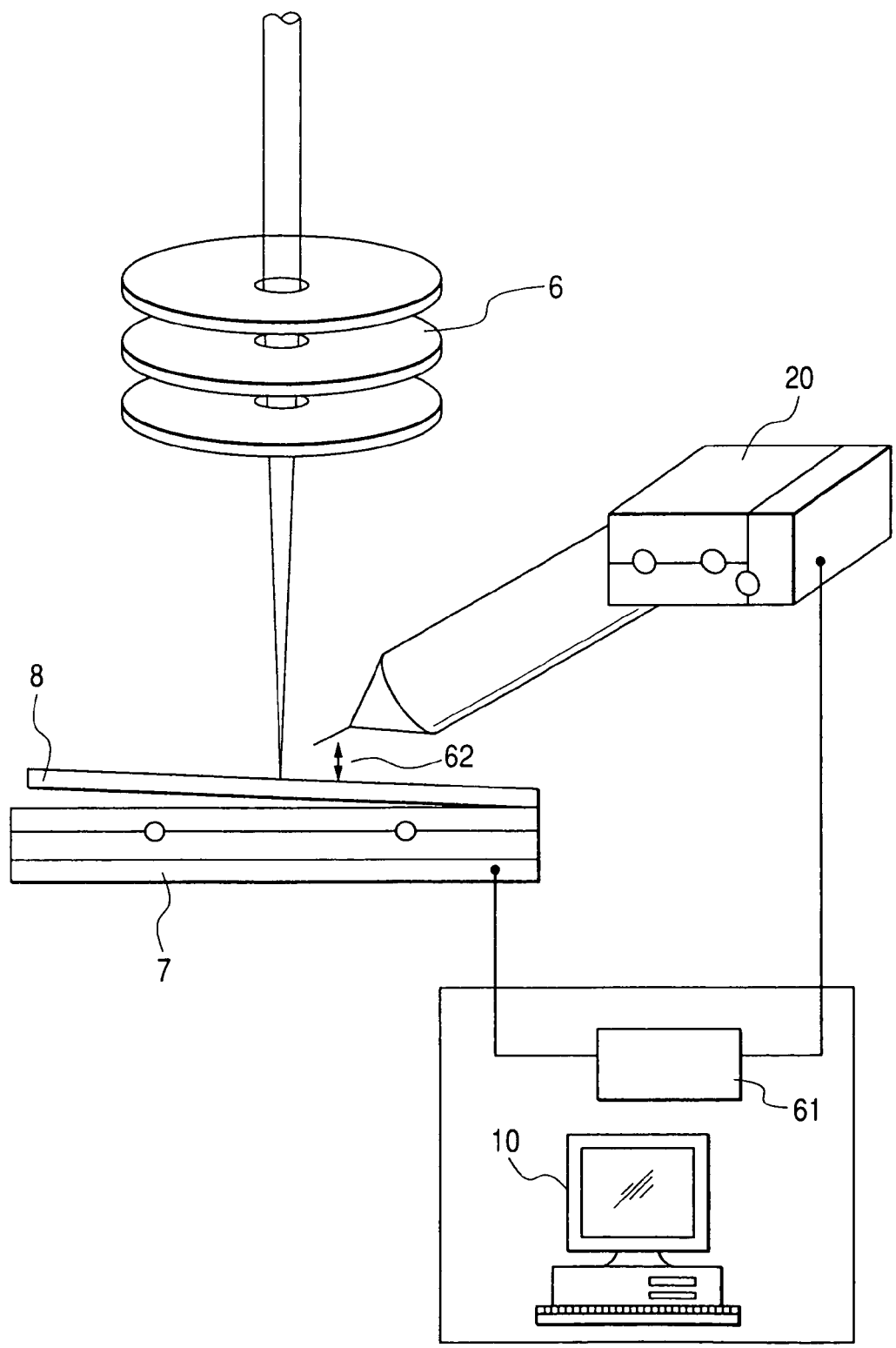
FIG. 13 is a diagram showing a method of controlling an electrode for preventing charging by a sample height recording unit.

FIG. 13 shows a charging control method in the case where the surface of the sample 8 is not parallel to the sample holder 7 in each of the first to third embodiments. In this case, when the sample holder 7 is moved to the right, the tip of the electrode 20 for preventing charging interferes with the surface of the sample. The tip of the electrode 20 for preventing charging is destroyed by collision with the sample 8 and the surface of the sample 8 is destroyed by collision with the electrode 20. If the interference is not avoided, the charging control by the electrode 20 for preventing charging is not effectively performed. A method of realizing both charge exchange between an irradiated area in the sample 8 and the electrode 20 for preventing charging and avoidance of the interference will be described hereinbelow.

FIG. 13 shows a first example of the method of realizing both charge exchange between the irradiated area in the sample 8 and the electrode 20 for preventing charging, and avoidance of interference. Before irradiation of a charged particle beam, a distribution of height of the whole surface of the sample 8 is recorded in a recording unit 61 of the controller 10. For example, in the case of setting a distance 62 of the tip of the electrode 20 for preventing charging to 100 μm, a precision of the height distribution of ±50 μm is necessary. In order to shorten the tip distance 62, precision of the height distribution has to be improved. A change in height which occurs when the sample holder 7 is moved is calculated by the recording unit 61 and the electrode 20 for preventing charging is moved only by the change amount, thereby making the tip distance 62 constant. For example, in the case where the tip distance 62 is 100 μm, the charged particle beam irradiated area is 100×100 μm², and the observation precision is 1 μm. In order to improve the observation precision, it is necessary to set the tip distance 62 to be short, and perform a charging control by the electrode 20 for preventing charging.

Figure 14:
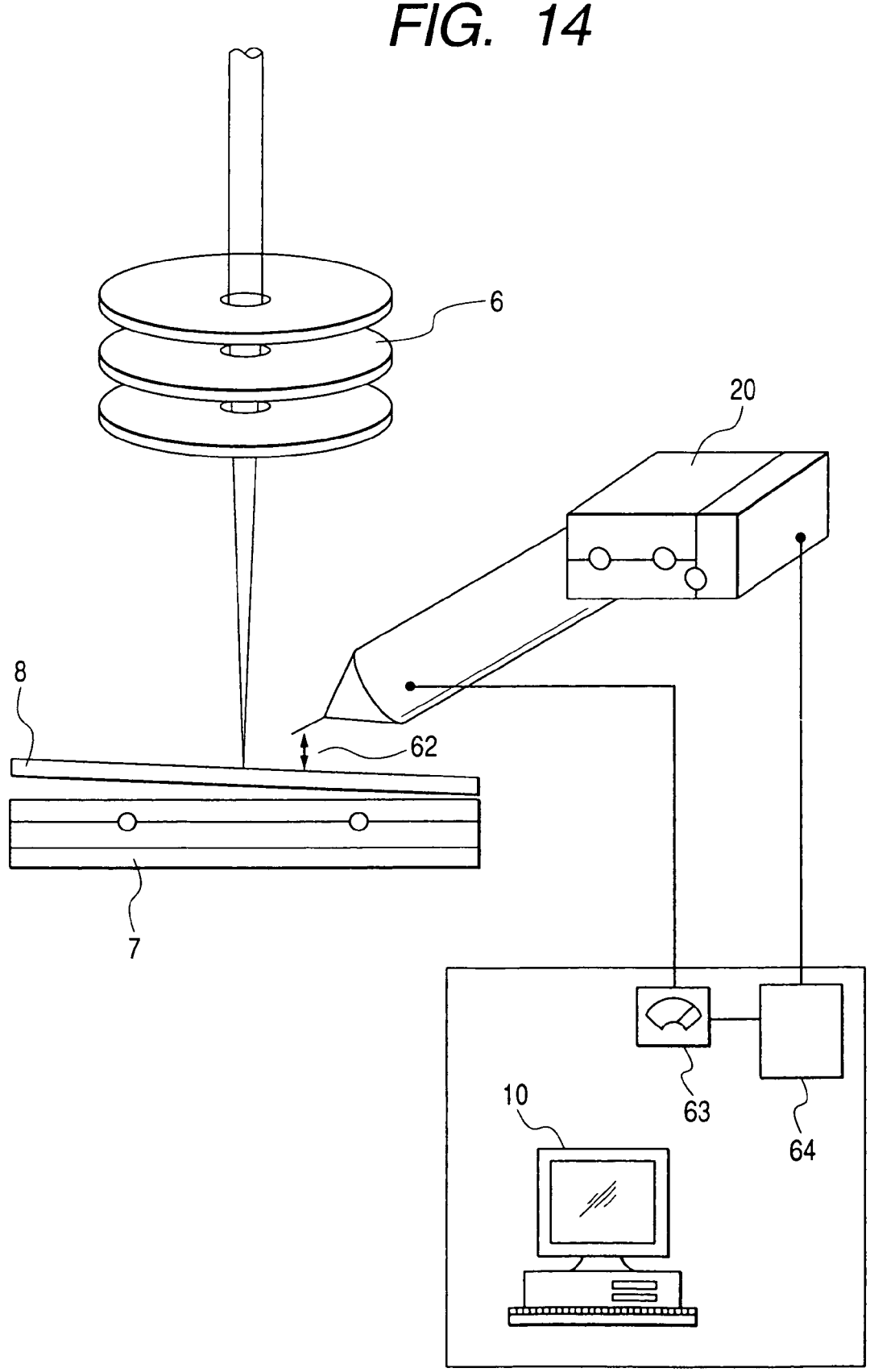
FIG. 14 is a diagram showing a method of controlling an electrode for preventing charging by a current flowing in the electrode.

FIG. 14 shows a second example of the method of realizing both the charge exchange between the irradiated area of the sample 8 and the electrode 20 for preventing charging and avoidance of interference. Different from the first example, according to the second method, a current flowing between the irradiated area and the electrode 20 for preventing charging is measured by a current meter 63 during a charging control. The current depends on the tip distance 62. When the electrode 20 for preventing charging approaches the sample 8 and the tip distance 62 becomes shorter, a current flowing in the electrode 20 increases. Consequently, the current is monitored so that the tip of the electrode 20 for preventing charging does not interfere with the surface of the sample during or after movement of the sample, the tip distance 62 is calculated by a calculating unit 64, and the electrode 20 for preventing charging is controlled so that the tip distance 62 becomes constant. For example, in the case where the tip distance 62 is 1 μm, the charged particle beam irradiated area is 1×1 μm², and observation precision is 10 nm. In order to improve the observation precision, the charging control has to be performed by either shortening the tip distance 62 or making the electrode 20 for preventing charges come into contact with the periphery of the irradiated area.

Figure 15:
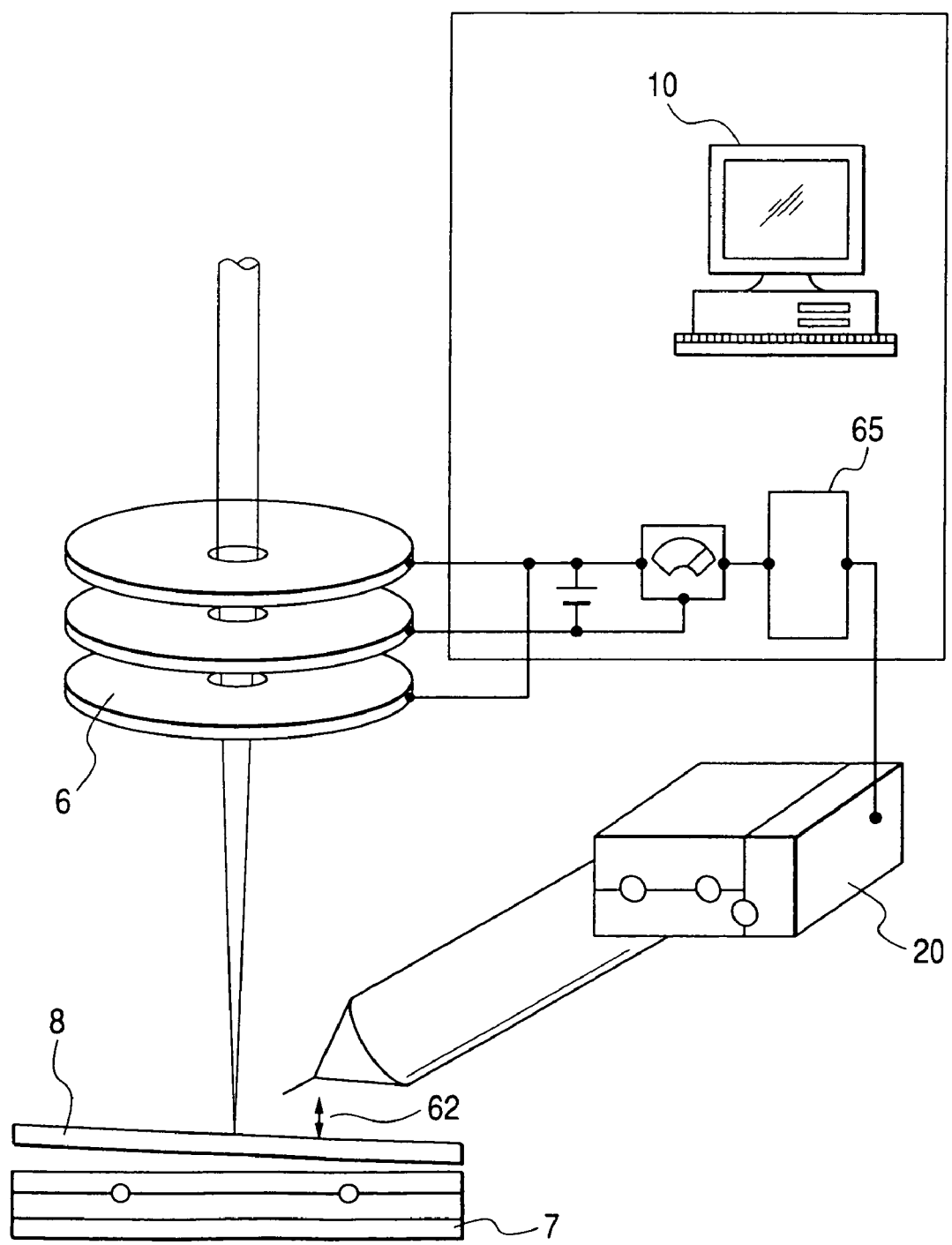
FIG. 15 is a diagram showing a method of controlling an electrode for preventing charging by a set value of an objective lens.

FIG. 15 shows a third example of the method of realizing both the charge exchange between the irradiated area of the sample 8 and the electrode 20 for preventing charging and avoidance of interference. Different from the foregoing two methods, the third method uses a set value of the objective lens 6. When the electrode 20 for preventing charging is in an escape position (for example, the tip distance 62 is 100 μm), the set value of the objective lens 6 is changed to adjust the focus point of the charged particle beam onto the surface of the sample 8. In this case, the controller 10 calculates the tip distance 62 by a calculating unit 65 from the change amount of the set value of the objective lens 6 to make the electrode 20 for preventing charging approach the surface of the sample. The control precision of the tip distance 62 by using the set value of the objective lens 6 is 30 μm.

Figure 16:
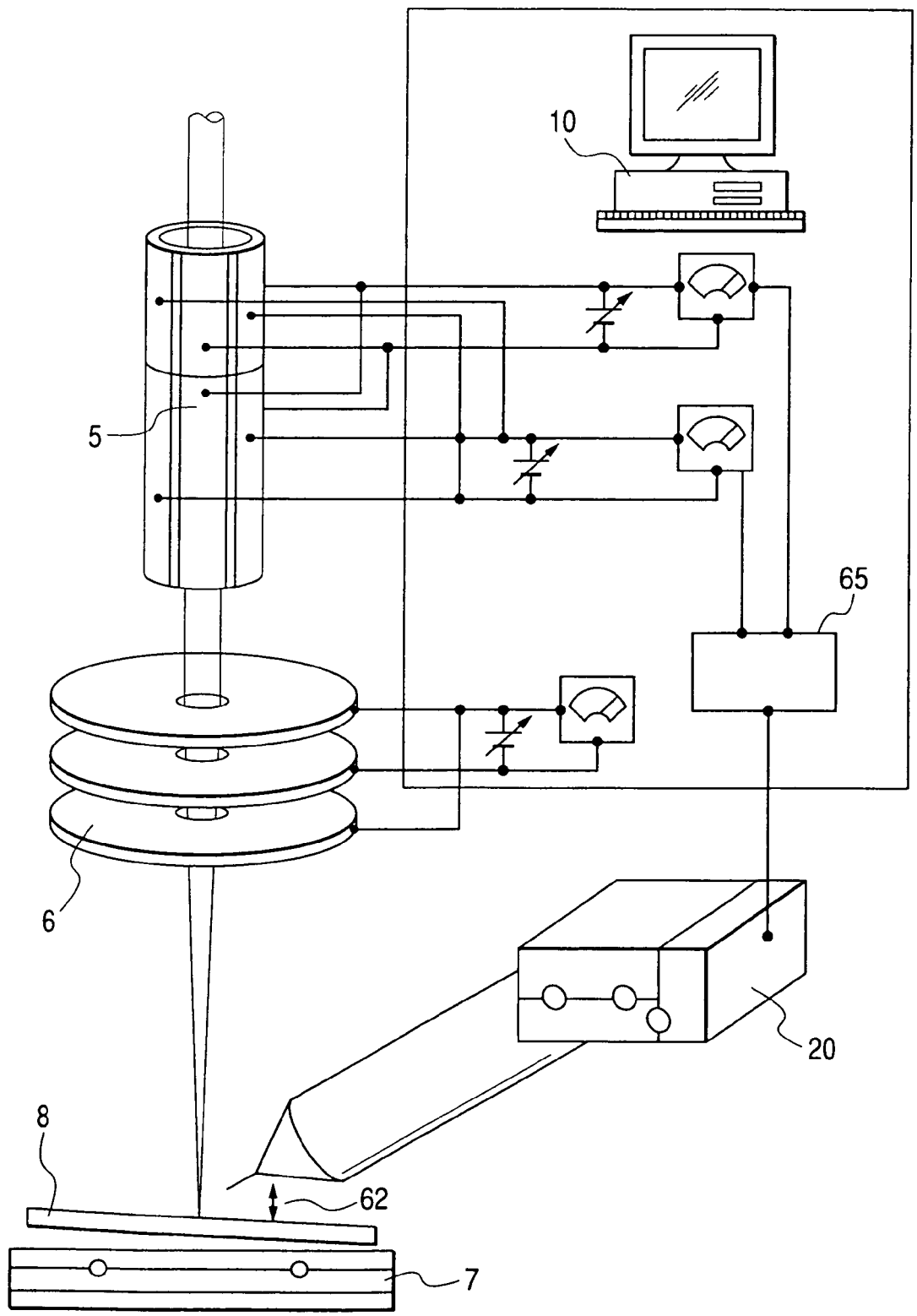
FIG. 16 is a diagram showing a method of controlling an electrode for preventing charging by a set value of a deflector.

FIG. 16 shows a fourth example of the method of realizing both charge exchange between the irradiated area in the sample 8 and the electrode 20 for preventing charging and avoidance of interference. The electrode 20 for preventing charging holds a single-axis movable mechanism in the direction of angles of 20 to 80 degrees with respect to the irradiation angle of the charged particle beam. The controller 10 sets the scan range of the charged particle beam into the deflector 5 and calculates the tip distance 62 corresponding to the scan range by the calculating unit 65 to thereby control the electrode for preventing charging. For example, in the case where the tip distance 62 is set to 30 μm, in a scan range of 30×30 μm², the observation precision is 0.3 μm, and processing precision is 0.5 μm.

In the case of conducting high-precision observation in a narrower scan range and, further, performing high-precision processing by referring to an observation image, at the time of changing the scan range, the tip distance 62 is automatically shortened in order to improve precision of both observation and processing. For example, in the case of setting the tip distance 62 to 1 μm, when the sample 8 is moved, the electrode 20 for preventing charging and the sample 8 interfere with each other. Consequently, the range in which the sample 8 can be moved on the sample holder 7 is set to 10 μm or less in the lateral direction.

The method can be combined with the method of realizing both charge exchange between the irradiated area in the sample 8 and the electrode 20 for preventing charging shown in FIGS. 13, 14, and 15 and avoidance of interference. In the case where the scan range is narrow (for example, narrower than 30×30 μm²), the electrode 20 for preventing charging is controlled by the method shown in FIG. 16. In the case where the scan range is wide, the electrode 20 for preventing charging is controlled by any of the methods shown in FIGS. 13, 14, and 15. In such a manner, the precision of observation of the charged particle beam and processing is dramatically improved.

Figure 17A:
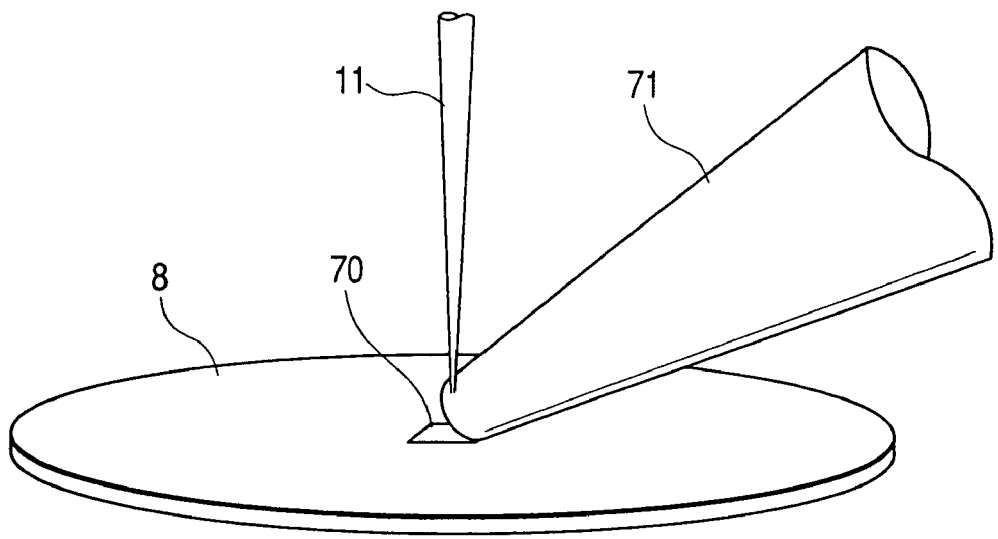
FIG. 17 is an explanatory diagram for comparing prior art 2 and an embodiment of the present invention.
Figure 17B:
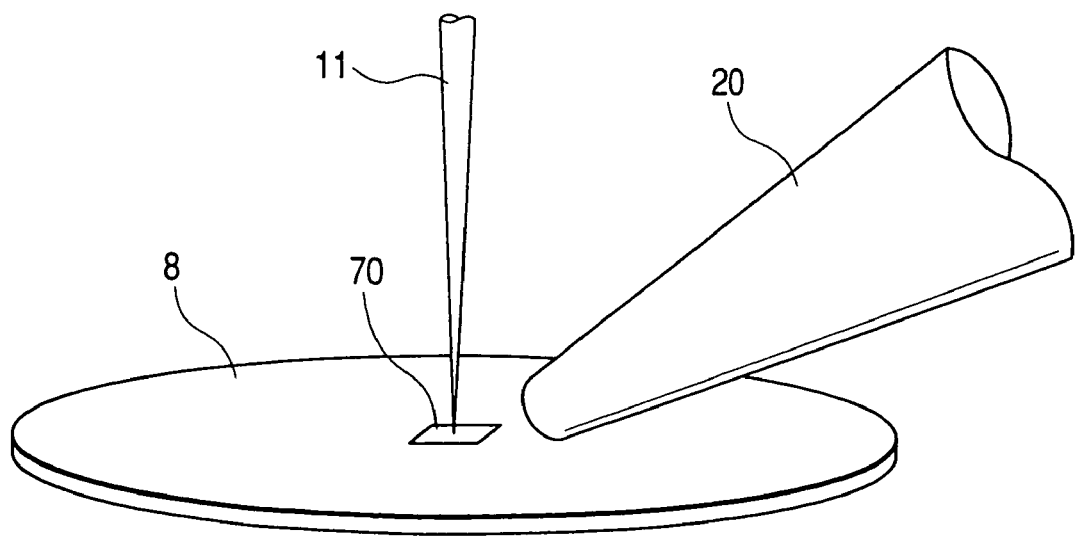

FIGS. 17A and 17B are explanatory diagrams for comparing the prior art 2 (FIG. 17A) and the embodiment of the invention (FIG. 17B). JP-A-8-138617 as the prior art 2 discloses a method of avoiding charge-up by forming a very thin conductive layer 70 near an irradiated area in the surface of a sample by irradiating an insulating film in the sample with an ion beam, and passing charges to the earth via a probe 71 which is allowed to come into contact with the conductive layer.

According to the method, when the probe 71 comes into direct contact with the conductive layer formed with the ion beam in a state where the ion beam irradiated area is narrower than the radius of the tip of the probe 71, as shown in FIG. 17A, the probe 71 overlaps with the irradiation area of the ion beam 11. However, in the embodiment, as shown in FIG. 17B, the probe 71 (electrode 20 for preventing charging) does not have to come into direct contact with the conductive layer 70 and does not overlap with the ion beam irradiated area.

As described above, in the apparatus for a charged particle beam according to the invention, by controlling charging by the electrode for preventing charging which is adjacent to or in contact with the surface of the sample, the charged particle beam is controlled with high precision. As a result, a process requiring experience and skill to suppress the charging of the surface of a sample is made unnecessary, and a secondary ion detector and an electron gun or ion gun are also made unnecessary. Thus, improved reliability of the charging control technique, reduced price of the apparatus, and observation, analysis, processing, and probe operation of higher precision can be realized.

The invention is summarized as follows.

(1) A method of preventing charging, comprising the steps of irradiating a sample mounted on a sample holder with a charged particle beam emitted from a charged particle source, and applying a predetermined voltage to an electrode for preventing charging disposed near a surface of the sample holder to generate an induced current between the electrode for preventing charging and an irradiated area in which charging occurs in the sample, thereby executing a control of preventing the charging without contact with the sample.

(2) A method of preventing charging, comprising the steps of irradiating a sample mounted on a sample holder with a charged particle beam emitted from a charged particle source, applying a predetermined voltage to an electrode for preventing charging disposed near a surface of the sample holder, and making the electrode come into contact with the sample to generate a current between the electrode for preventing charging and an irradiated area in which charging occurs in the sample, thereby executing a control of preventing the charging.

(3) A method of preventing charging according to the configuration (1) or (2), wherein the surface of the sample is observed with the charged particle beam, the electrode for preventing charging is made come into contact with the periphery of the irradiated area, and the charging preventing control is performed.

(4) A method of preventing charging according to the configuration of (1) or (2), wherein the electrode for preventing charging is constructed so as to be movable with respect to the surface of the sample.

(5) A method of preventing charging according to the configuration of (1) or (2), wherein a voltage of −5V to +5V is applied to the electrode for preventing charging.

(6) A method of preventing charging according to the configuration of (1), (2), or (3), wherein the sample contains an insulating material.

(7) A method of preventing charging, comprising the steps of irradiating a sample containing an insulating material mounted on a sample holder with a charged particle beam emitted from a charged particle source, and applying a predetermined voltage to an electrode for preventing charging disposed near a surface of the sample holder, thereby executing a control of preventing the charging which occurs in the irradiated area in the sample without contact with the sample.

(8) An apparatus for a charged particle beam having: a charged particle source; a charged particle optical system for focusing and deflecting a charged particle beam emitted from the charged particle source; a detector for detecting secondary particles emitted from a sample irradiated with the charged particle beam; and a sample holder on which the sample is mounted, the apparatus comprising: an electrode for preventing charging which is provided so as to be movable with respect to the surface of the sample holder; and a controller for the electrode for preventing charging, for controlling a voltage to be applied to the electrode for preventing charging and the movement, wherein a control for preventing the charging is performed by generating an induced current or a current between an irradiated area in the sample, which is irradiated with the charged particle beam, and the electrode for preventing charging.

(9) An apparatus for a charged particle beam according to the configuration of (8), wherein the electrode for preventing charging is disposed between the charged particle optical system and the sample holder and is provided movably with respect to the surface of the sample holder.

(10) An apparatus for a charged particle beam according to the configuration of (8), wherein the electrode for preventing charging takes the form of an electrode made of a conductive material and fabricated in a needle shape having a tip whose curvature is 100 µm or less.

(11) An apparatus for a charged particle beam according to the configuration of (8), wherein a voltage from −5V to +5V is applied to the electrode for preventing charting.

(12) An apparatus for a charged particle beam according to the configuration of (8), wherein the controller for the electrode for preventing charging has a calculating unit for calculating a control value of the position of the electrode for preventing charging or a voltage on the basis of a change in a current flowing between the irradiated area and the electrode for preventing charging during the control of preventing charging.

(13) An apparatus for a charged particle beam according to the configuration of (8), wherein the controller for the electrode for preventing charging has a calculating unit for calculating a distance between the electrode for preventing charging and the sample or a voltage on the basis of a set value of the lens or the deflector.

(14) An apparatus for a charged particle beam, having: a charged particle source; a lens for focusing a charged particle beam emitted from the charged particle source; a deflector; a detector for detecting secondary particles emitted from a sample irradiated with the charged particle beam; and a sample holder for holding the sample; and a sample position controller for controlling the position of the sample holder, the apparatus including: a first electrode (for example, electrode for preventing charging) which is provided between the charged particle beam irradiated area in the sample and the lens so as to be movable with respect to the sample and generates an induced current or a current between the electrode and the charged particle beam irradiated area; an electrode controller controlling the first electrode and driving independent of the sample position controller, and a second electrode (for example, probe manipulator) driving independent of the sample holder position controller and generating a current between the second electrode and the charged particle beam irradiated area, wherein a control for preventing the charging in the charged particle beam irradiated area which is charged, by using the first and second electrodes.

The invention realizes the apparatus for a charged particle beam, with improved reliability of control on the charged particle beam and the probe and generally excellent analysis and sample fabricating efficiency by eliminating necessity of experience and skills in the technique of preventing charging in the apparatus for a charged particle beam.

What is claimed is:

1. A specimen fabrication method comprising:
    irradiating an ion beam to a sample,
    contacting a probe to a surface of the sample,
    applying a predetermined voltage to the probe,
    separating the probe from the sample,
    manufacturing a specimen from the sample by irradiating the ion beam to the sample again after separating the probe from the sample,
    approaching a tip of the probe which is separated from the sample to the specimen,
    connecting the probe and the specimen, and
    fixing the specimen on a mesh holder.

2. The specimen fabrication method according to claim 1, the probe and the specimen are connected by a deposition gas released from a gas nozzle.

3. The specimen fabrication method according to claim 2, the gas nozzle is an electrode for neutralization.

4. The specimen fabrication method according to claim 2, a charge of the specimen is prevented by the step of approaching an electrode to the specimen.

5. The specimen fabrication method according to claim 1, further comprising the steps of:
    detecting secondary particles emitted from the sample by the irradiation of the ion beam.

6. The specimen fabrication method according to claim 5, further comprising the steps of:
    displaying a second particle image on a display based on a detected signal of a detector.

7. The specimen fabrication method according to claim 6, wherein a contact position of the probe is decided based on the image which is displayed on the display.

8. The specimen fabrication method according to claim 6, wherein a manufacturing position is decided based on the image which is displayed on the display.

9. The specimen fabrication method according to claim 1, further comprising the steps of:
    controlling driving of the probe and applying a voltage to the probe.

10. A specimen fabrication method comprising:
    irradiating an ion beam to a sample mounted on a sample stage,
    contacting a probe to a surface of the sample,
    applying a predetermined voltage to the probe,
    separating the probe from the sample,
    tilting the sample stage with respect to an optical axis of the ion beam,
    manufacturing a specimen from the sample by irradiating the ion beam to the sample again after separating the probe from the sample,
    returning the sample stage to a state before the tilting,
    approaching a tip of the probe which is separated from the sample to the specimen,
    connecting the probe and the specimen, and
    fixing the specimen on a mesh bolder.

* * * * *